United States Patent
Kahle

(10) Patent No.: US 6,881,583 B2
(45) Date of Patent: Apr. 19, 2005

(54) WATER CHLORAMINATION CONTROL SYSTEM

(75) Inventor: Scott J. Kahle, Hartland, WI (US)

(73) Assignee: Applied Spectrometry Associates Inc., Waukesha, WI (US)

( * ) Notice: Subject to any disclaimer, the term of this patent is extended or adjusted under 35 U.S.C. 154(b) by 117 days.

(21) Appl. No.: 10/172,869

(22) Filed: Jun. 16, 2002

(65) Prior Publication Data

US 2003/0232447 A1 Dec. 18, 2003

(51) Int. Cl.[7] ............................................. G01N 33/00
(52) U.S. Cl. ........................ 436/113; 436/125; 436/55; 436/164
(58) Field of Search ......................... 436/55, 113, 125, 436/164; 422/1, 3, 37; 210/749, 754, 7

(56) References Cited

U.S. PATENT DOCUMENTS 6,315,950 B1    11/2001   Harp et al.

FOREIGN PATENT DOCUMENTS

| JP | 10028981 A | * | 2/1998 | ............ C02F/1/76 |
| WO | WO 9735191 A1 | * | 9/1997 | .......... G01N/33/18 |

OTHER PUBLICATIONS

Cloramin.2 "Physical and Chemical Properties" http://www.epa.gov/ncea/pdfs/drinkchapter2.pdf, Mar. 8, 1994.*
Valentine et al. "A spectrophotometric study of the formation of an unidentified monochloramine decomposition product", Wate Research, 1986, v. 20, No. 8, pp. 1067–1074.*
Scott J. Kahle et al the use of Multiple Wavelength Ultra-violet–Visible Absorbance Spetrometry for on–Line Analysis of Wastewater Process Samples Undated.
Standard methods of Water and Waste Water Analysis 204 Edition p 4–78–4–79 & p 4–45–4–46.
Water Chloramination Process Control Nov. 1997.

* cited by examiner

Primary Examiner—Yelena G. Gakh
(74) Attorney, Agent, or Firm—Jeffrey W. Sainio

(57) ABSTRACT

A water chloramination control system compares the concentration of aqueous higher chloramines to aqueous ammonia to optimize the ratio of added ammonia to chlorine. Aqueous ammonia concentration is measured by conversion to monochloramine which concentration is determined spectroscopically. Higher chloramine concentration is measured by a reaction producing free iodine which concentration is also determined spectroscopically. The higher chloramine to ammonia ratio is used to control ammonia feed to the water. Problems associated with excess chlorine, or excess ammonia, are avoided.

16 Claims, 7 Drawing Sheets

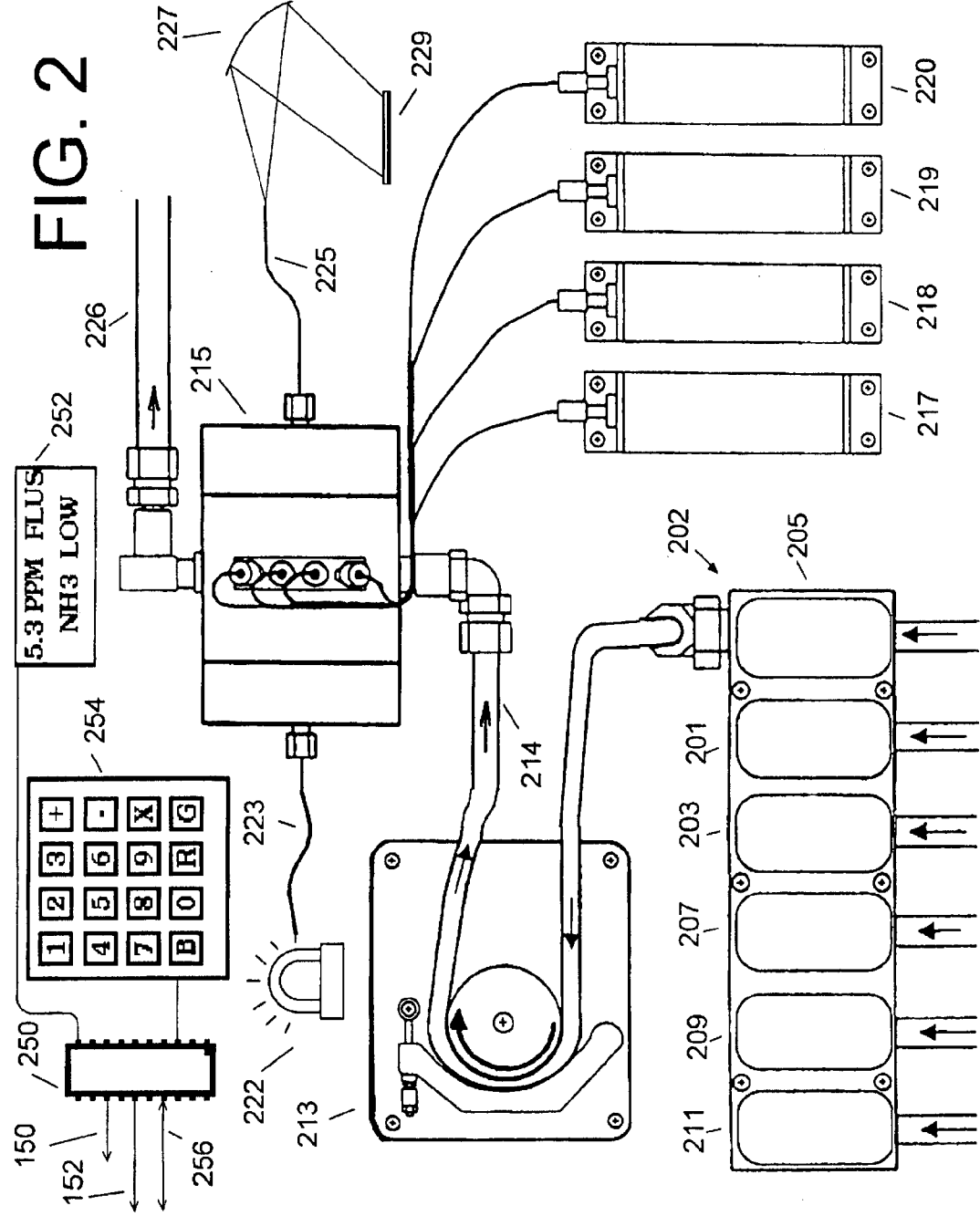

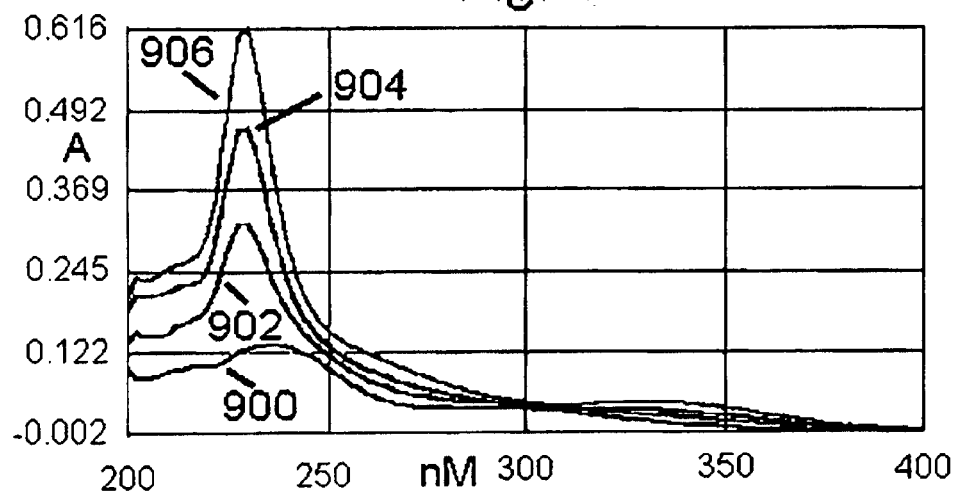
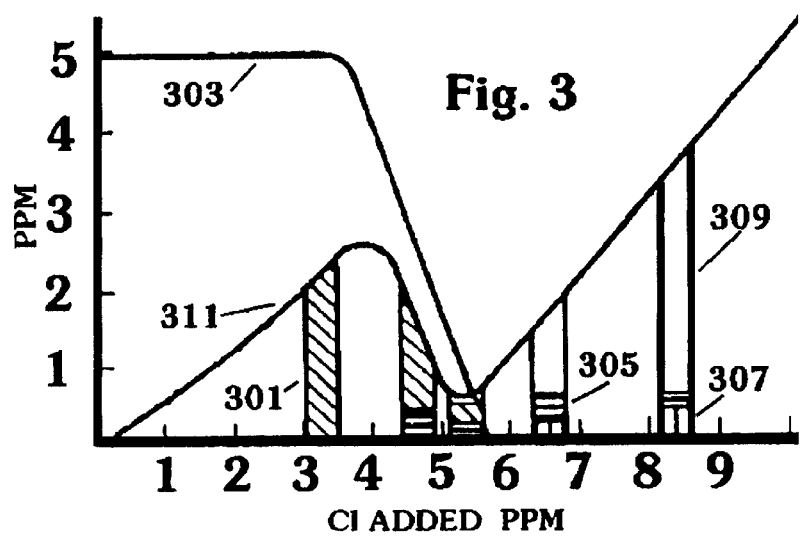

WATER CHLORAMINATION CONTROL SYSTEM

FIELD OF THE INVENTION

The present invention relates generally to a system and method for controlling chlorination of water, typically drinking water. More particularly, the invention relates to control of ammonia feed with respect to chlorine feed to minimize the concentration of ammonia or higher chloramines in the water.

BACKGROUND OF THE INVENTION

Chlorine has disinfected water supplies for hundreds of years. Such water is not generally pure; the water may contain harmful bacteria; innocuous proteins such as from decaying leaves; chlorine-reactive ions of iron, sulfide, and nitrite; and hard-water compounds such as magnesium or calcium carbonate. As community water supplies have expanded in scale, accurate and reliable automated chlorination control systems have become preferred. Underchlorination runs the risk of disease; overchlorinated water is distasteful and reacts to natural organic matter (NOM) to form chlorinated organic matter (also known as trihalomethanes, or THM). Recently, the U.S. Environmental Protection Agency has reduced allowable concentrations of THMs, which are known carcinogens.

Chlorine is typically added to water in elemental form as $Cl_2$. Chlorine in water is quickly converted to hypochlorous acid which dissociates to $H^+$ and $OCl^-$.

$$Cl_2 + H_2O < - - - > HCl + HOCl < - - - > 2H^+ + OCl^- + Cl^- \quad \text{(Eq. 1)}$$

Chlorine may also be added in other forms, such as calcium hypochlorite. The unmodified term "chlorine" is used to encompass $Cl_2$, $HOCl$, or $OCl^-$. By adding ammonia as well as chlorine, monochloramine ($NH_2Cl$) is the desired result; it is a less aggressive oxidizer less likely to attack metals such as structural steel and toxic lead in the distribution pipes, is longer-lasting, and less reactive with NOM.

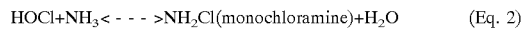

$$HOCl + NH_3 < - - - > NH_2Cl(\text{monochloramine}) + H_2O \quad \text{(Eq. 2)}$$

The unmodified term "ammonia" is used to encompass $NH_3$ or $NH_4^+$, the ammonium ion resulting from hydrolysis. Monochloramine has about 25 times the disinfecting power of the $OCl^-$ ion due in part to its neutral charge which more easily penetrates bacterial cell walls. But a simple addition of a 1:1 molar ratio of chlorine and ammonia is not optimal; variables such as chlorine consumed by water impurities such as iron, pH, temperature, natural aqueous ammonia, and contact time all affect the optimal amount of chlorine, and therefore the desired chlorine: ammonia feed ratio. If ammonia is overfed, excess nitrogen is a food source for undesirable bacteria in the water distribution system. If ammonia is underfed, dichloramine or at higher Cl:N ratios, even trichloramine is produced from monochloramine:

$$HOCl + NH_2Cl < - - - > NHCl_2(\text{dichloramine}) + H_2O \quad \text{(Eq. 3)}$$

$$2NH_2Cl(\text{acid-catalyzed}) < - - - > NHCl_2 + NH_3 \quad \text{(Eq. 4)}$$

$$HOCl + NHCl_2 < - - - > NCl_3(\text{trichloramine}) + H_2O \quad \text{(Eq. 5)}$$

Trichloramine is less commonly but more accurately known as nitrogen trichloride. The higher chloramines, dichloramine and trichloramine, have unacceptable pungent taste and odor and are less effective disinfectants. The chlorine in uncombined form or monochloramine is known as available or 'residual' chlorine. Chlorine, hypochlorous acid, hypochlorite ion, monochloramine, dichloramine, and trichloramine are collectively referred to as chlorination compounds. The acid-catalyzed reaction of monochloramine with itself (Eq. 4) to form dichloramine and ammonia, is known as a disproportionation reaction.

In a control system, a desirable control signal is one which linearly achieves a low level to indicate the controlled variable should be lowered, and a high level to indicate the controlled variable should be raised. But chlorination is not properly controlled by simply measuring the resultant chlorine concentration. A major problem is that available chlorine concentration does not rise monotonically as more chlorine is added. (For clarity, the discussion of chlorine:ammonia ratios in this and the next three paragraphs will ignore the variables of consumption, pH, temperature, and contact time, which affect the actual optimal ratios.) When the molar chlorine:ammonia ratio exceeds 1:1, the available chlorine concentration actually decreases, due to competing reactions forming higher chloramines, dropping by over 75%, until a chlorine:ammonia ratio of about 1.7:1 is reached. Above this ratio, saturation occurs and available chlorine concentration rises again. A similar problem occurs if the monochloramine concentration is monitored; at higher chlorine:ammonia ratios, monochloramine concentration actually decreases due to conversion to dichloramine and trichloramine. Neither measuring available chlorine, or monochloramine, provides a linear or even monotonic control indicator over the desired range.

Conventional strategies for controlling the chlorine:ammonia ratio fall into two common methods:

1. A very small ammonia concentration is maintained to ensure that monochloramine is the predominant chlorine species. However in practicality, control of ammonia at levels on the range of tens of parts per billion is difficult, nearing the detection limit of the analyzer. An excess ammonia concentration must be maintained, simply to stay in the detection range of the analyzer.

2. The chlorine:ammonia is controlled to a molar 1:1 ratio or below. If correctly done, the predominant chlorine species is monochloramine. Unfortunately, aqueous ammonia already present, or ions consuming chlorine, alter this ratio. If chlorine of overfed, both available chlorine and ammonia decrease and not at the same rate, leading to incorrect control decisions. Conventional analyzers for this method measure monochloramine concentration. But monochloramine concentration actually decreases as the chlorine:ammonia ratio exceeds 1:1, again leading to incorrect control decisions.

U.S. Pat. No. 6,315,950, issued Nov. 13, 2001 to Harp et al., discloses a system for the measurement of monochloramine, and $Cl:NH_3$ control to a molar 1:1 ratio or below. Monochloramine is reacted with phenol compounds, using a nitroferricyanide catalyst, to form indophenols, which are detected by their absorbance in the 600–800 nanometer (nM) range. Multiple analyzer cells are used to measure free ammonia, total ammonia, and monochloramine. The process uses toxic chemicals, and produces toxic waste. In practice, the analysis time of about 20 minutes, is excessive for many control system applications.

Multiple analyzer cells add cost to an analysis system, and also exhibit differential drift. If one cell has a sensitivity gain, the resultant ratios of its measurements compared to the results of another cell, are artificially inflated. Calibration and nulling become onerous, or accuracy suffers. If a single cell is utilized, a sensitivity gain yields an increase in both measurements, which tends to null out comparison errors.

A water-analysis system may employ ultraviolet (UV) spectroscopy. With two exceptions in the infrared, water is transparent to wavelengths from 200 to 1400 nM. But some dissolved chemicals will absorb certain wavelengths; each chemical has a particular absorbance pattern, or signature, whose strength is proportional to its concentration. With repeatable illumination and spectrum collections of a sample, a blank spectrum is taken; a chemical added to initiate a reaction resulting in a product; the product spectrum is taken; the blank spectrum subtracted from the product spectrum; and the difference spectrum is analyzed to determine the product's identity and concentration. The spectrum is produced by a monochromator, which may operate through prismatic, diffractive, holographic, optical filtering, or other means. Analysis of more spectrum points generally provides greater accuracy and better isolation from extraneous absorbance generated by various contaminants. Subtraction of spectra is performed in accordance with Beer's Law; optical absorbances are subtracted, where absorbance is defined as the negative log of the light intensity.

UV spectrometers used for such analysis typically include a UV light source; an analyzer cell directly or indirectly illuminated by the UV light, and plumbed to the sample water and various sources of liquid reagents; a UV light collection mechanism which receives the UV light transmitted through the sample; a monochromator to produce and focus the UV spectrum; an array detector which produces an electrical signal representative of the spectrum; an analog-to-digital converter which converts the electrical signal to digital data; and a microprocessor which performs math, control, and logic operations, including calculation of chemical concentrations, sequential operation of the analyzer hardware, control of external valves, and communications to operators, recorders, or other systems.

Some chemicals, such as ammonia, do not have reliable absorbance characteristics. To be measured with spectroscopy, these chemicals must be converted to another chemical with a reliable spectrum.

There is a need for a water chlorination control system which is capable of measurement in the desired range; exhibits accuracy and stability over a wide range of chlorine:ammonia ratios; maintains a minimum concentration of both ammonia and dichloramine; may also maintain a desired amount of monochloramine; requires no toxic-chemical handling; uses a minimum of analyzer cells, preferably a single analyzer cell; and has sufficient speed to operate in a control environment.

SUMMARY OF THE INVENTION

A preferred chlorination control system recognizes that an ammonia overfeed produces excess free ammonia with little higher chloramines, an ammonia underfeed produces excess higher chloramines with little free ammonia, and that these two conditions cannot coexist. Comparing the higher chloramine concentration to the ammonia concentration, yields a balance indication of chlorine to ammonia, avoiding the nonmonotonic measurement problems associated with chlorine or monochloramine alone. Such a preferred system is referred to as a chloramination control system. With optimal chlorine:ammonia balance determined, underchloramination (as preferably measured by monochloramine concentration) may be corrected by increasing both chlorine and ammonia, and conversely, overchloramination corrected by decreasing both chlorine and ammonia.

The preferred embodiment of the present invention utilizes the comparison of higher chloramines to ammonia as an ammonia feed signal, where an increase in this signal indicates a need for an increase in the ammonia to chlorine ratio in the water, and a decrease in this signal indicates a need for an decrease in the ammonia to chlorine ratio in the water. This signal is monotonic over a wide ratio of ammonia and chlorine feeds, can be determined within the detection range of practical detectors, with a single analyzer cell, without the production of toxic waste, in a timespan adequate for control applications. With the ammonia to chlorine ratio optimized, monochloramine concentration may be measured, and controlled by adjusting both ammonia and chlorine feed.

Features and advantages of the invention will become apparent to these of ordinary skill in the art upon review of the following drawings, detailed description and claims.

BRIEF DESCRIPTION OF THE DRAWINGS

FIG. 2 shows a block diagram of a water analyzer.

FIG. 3 illustrates the relationship of ammonia, available chlorine, free chlorine, monochloramine, dichloramine, and trichloramine over a range of Cl:NH$_3$ feed ratios.

FIG. 9 shows a spectrum of trichloramine over a range of concentrations.

Figure 1:
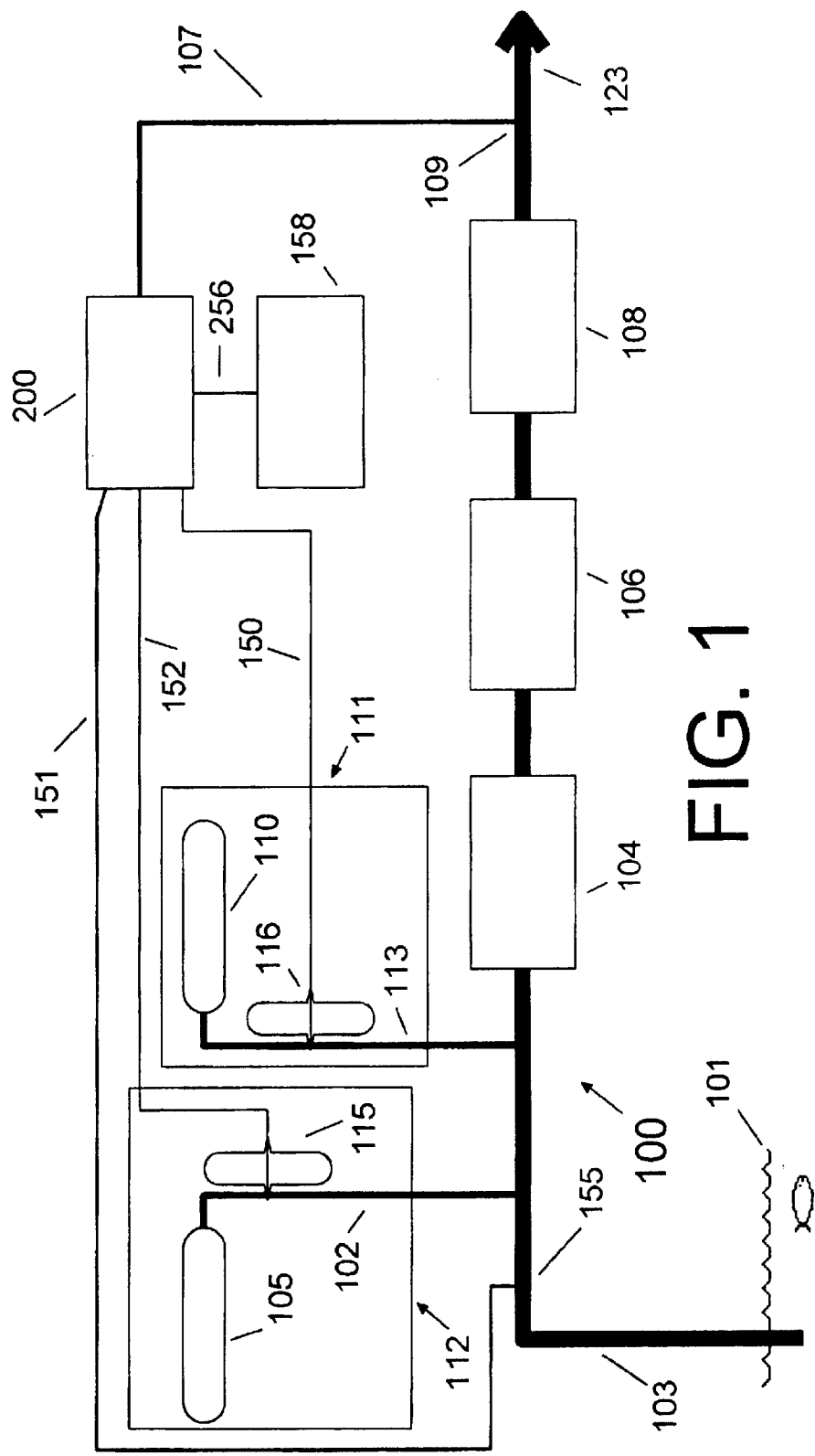
FIG. 1 shows a block diagram of a water chlorination plant.

Before one embodiment of the invention is explained in detail, it is to be understood that the invention is not limited in its application to the details of construction and the arrangement of components set forth in the following description or as illustrated in the drawings. The invention is capable of other embodiments and of being practiced or being carried out in various ways. Also, it is to be understood that the phraseology and terminology used herein is for the purpose of description and should not be regarded as limiting. In particular, the common practice of water treatment plants is to maintain a constant chlorine feed, and vary the ammonia feed in response to system changes. For best understanding of the invention by those skilled in the art, the best mode of the invention is disclosed in accordance with this common practice. However, the invention is not limited to balance via a constant-chlorine feed with variable ammonia feed; balance may be achieved by variable chlorine feed and constant ammonia feed, or some combination of these methods. Also, chlorine may be supplied to the water supply by elemental chlorine, or in other forms such as sodium hypochlorite.

DETAILED DESCRIPTION OF THE PREFERRED EMBODIMENT

FIG. 1 illustrates a water chlorination plant 100. Water 101 in the form of a river, lake, underground aquifer, well, or other source, is pumped through pipe 103 to the plant 100. A chlorine feed system 112 comprises chlorine source 105, such as a chlorine tank, feeding chlorine through chlorine feed line 102, controlled by chlorine control valve 115, into the water. An ammonia feed system 111 comprises ammonia source 110, such as an ammonia tank, which feeds ammonia through ammonia feed line 113, controlled by ammonia feed valve 116, into the water. The water may receive additional processing such as aeration 104, filtration 106, or fluoridation 108, and exits the plant 100 through pipe 123 to a municipal water supply or other customer. Programmable-logic-controller (PLC) 158 provides overall control of the chlorination plant 100.

Sample line 107 brings a sample of the outgoing water from sample point 109 to analyzer 200, which computes an ammonia feed signal 150 controlling ammonia feed valve 116. Sample line 151 brings a sample of the incoming water from sample point 155 to analyzer 200. Sample point 155 may also be downstream of the chlorine feed system 112. Analyzer 200 may also compute a chlorine feed signal 152 controlling chlorine control valve 115.

FIG. 2 illustrates the water analyzer 200. Manifold assembly 202 contains a sample input valve 203, air valve 205, ammonia calibrate input valve 207 inputting a known concentration of ammonia, chloramine calibrate valve 201 inputting a known concentration of higher chloramines, clean valve 209 inputting a cleaning solution, and zero input valve 211 inputting a transparent fluid such as deionized water. Generally, at most one valve is opened. Fluid from the open valve is pumped by peristaltic pump 213 through hose 214 into analyzer cell 215. Outgoing fluid exits through drain line 226.

Analyzer cell 215 is illuminated by xenon strobe 222 through incoming quartz fiber optic cable 223. Light not absorbed in the analyzer cell, enters outgoing quartz fiber optic cable 225 to monochromator 227 whose spectrum strikes array sensor 229. Sensor array 229 generates a multiplicity of signals for a multiplicity of points, for instance 256 points, each point's signal representing the intensity of light at a particular wavelength of light received from the analyzer cell 215. The wavelengths may range, for instance, from 200 to 450 nM. The signals are input to the processor 250, typically by conversion from analog voltages to digital codes which are then read serially by the processor 250 and subsequently analyzed.

The analyzer cell 215 receives a NaOH-EDTA solution from alkali injector pump 217, NaOCl solution from chlorine injector pump 218, a KI solution from iodide injector pump 219, and acid from $H_2SO_4$ injector pump 220. Processor 250 may be a microprocessor, microcontroller, or other system performing arithmetic, logic, control, and input/output functions. Processor 250 provides overall control of the analyzer, controlling the various valves on manifold assembly 202, injector pumps 217–220, peristaltic pump 213, firing control of strobe 222, and receives electrical signals representative of the light striking array sensor 229. Processor 250 computes chemical concentrations based on the light striking array sensor 229 and outputs an ammonia feed signal 150; and may display control, diagnostic, and analytic data on display 252, receive commands through keypad 254, and communicate to other systems such as PLC 158 through serial IO line 256. Ammonia feed signal 150 may be an analog voltage controlling a valve which controls ammonia feed into the water supply, or the ammonia feed signal may be implemented as a command message on IO line 256, or a variety of other implementations. Alternatively to, or in conjunction with controlling ammonia, chlorine concentration may be controlled through chlorine feed signal 152, as a command message on IO line 256, or other methods as are known in the art.

A major function of the analyzer 200 is to determine the ratio of chlorination compound concentration to ammonia concentration. The relationship of chlorine, monochloramine, dichloramine, and trichloramine, at an initial 5 ppm molar ammonia concentration, is shown in FIG. 3. Monochloramine concentration 301 (diagonal shading) peaks around 2 parts per million (PPM) at 3 PPM chlorine. Ammonia plus monochloramine concentration 303 drops to nearly zero, then rises very slightly as chlorine concentration increases. Dichloramine concentration 305 (horizontal shading) peaks to 0.5 PPM around 4.5 PPM chlorine, then drops. Trichloramine concentration 307 (vertical shading) is negligible except approaching about 0.5 PPM as 7 PPM chlorine is reached. Free chlorine 309 (no shading) rises after 5 PPM Cl is added. Available chlorine 311 peaks around 4 PPM, drops to a minimum around 5.5 PPM, then rises again. The available chlorine minimum is less dramatic if significant proteinaceous nitrogen is present. Past 5.5 PPM, chlorine exists mostly as disagreeable higher chloramines and carcinogen-forming free chlorine.

Figure 4:
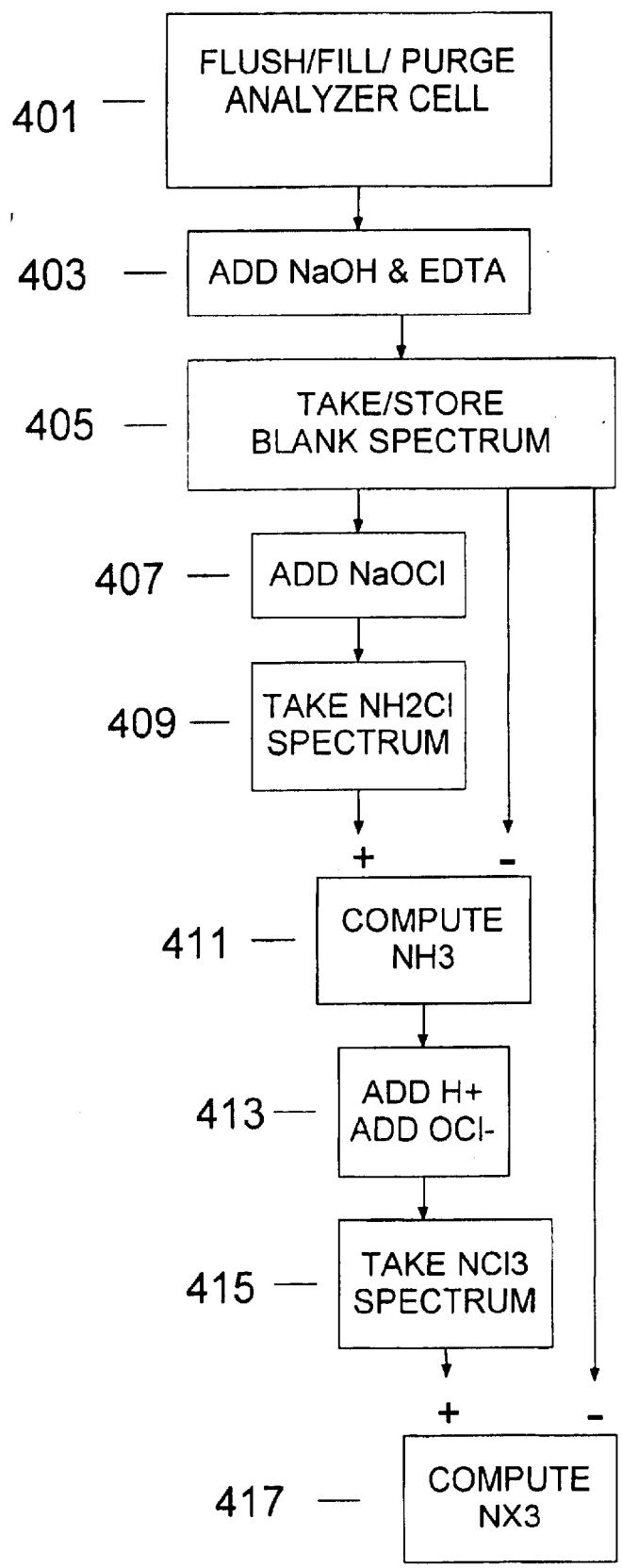
FIG. 4 shows a flowchart of the process for determining ammonia concentration.

With reference to FIG. 4, ammonia is measured by converting it to monochloramine. At pH of at least 8, $NH_4^+$ is forced to $NH_3$ and chlorine combines with $NH_3$ to produce monochloramine quickly, completely, and exclusively, with no dichloramine or tirichloramine production within the sampling time, even at molar ratios of 20:1 or more. The monochloramine is then measured spectroscopically under processor control. The pH is then dropped to 3 or below. At this pH with excess chlorine, ammonia, monochloramine, and dichloramine are all converted to trichloramine. The trichloramine concentration is then measured spectroscopically under processor control, which concentration represents the concentration of ammonia plus monochloramine plus dichloramine plus trichloramine (A+M+D+T).

To detail, in step 401, the analyzer cell 215 is flushed with sample water from valve 203 using roughly one liter of water, and the incoming line to the analyzer is purged of liquid by pumping an excess of air through valve 205 into the analyzer cell 215. The flushing also ensures that stale water, not representing the current exiting plant water, in sample line 107 is discarded.

In step 403, alkali such as NaOH is added to the sample by pump 217 to raise the pH to 8 or above. If the incoming water is known to contain excess hardness, a complexing agent such as EDTA (ethylene diamine tetra-acetate), is added to bind the offending minerals to avoid precipitation that would foul the optical path. An NaOH/EDTA solution may be prepared by mixing 500 grams of NaOH pellets and 250 grams of EDTA with 10 liters of deionized water. The peristaltic pump 213 spins slowly to bubble air from valve 205 through the sample for mixing, and a delay of roughly 10 seconds delay provides bubble clearing and complete mineral complexing to the EDTA.

In step 405, a blank spectrum is collected and stored as a reference. Any monochloramine already in the water is nulled by this step. If the monochloramine concentration is desired, this blank spectrum may be compared to a spectrum of incoming water from valve 201 plus NaOCl from pump 218, and analyzed to determine the monochloramine concentration (M). As these spectra are not of the same water sample, the resultant M concentration data are somewhat noisy.

In step 407, an excess of NaOCl reagent is added with pump 218 and mixed by again bubbling air. The NaOCl reagent may be prepared by mixing 1.5 liters of a 5% NaOCl solution in 8.5 liters of deionized water. A preferred source for the NaOCl solution is common household bleach, such as Clorox brand Blue Label bleach. A reaction time of typically ten seconds is allowed for monochloramine to form. In water containing large amounts of ammonia (i.e. wastewater), reaction times of up to two minutes are required for the ammonia to convert to monochloramine.

In step 409, a monochloramine sample spectrum is collected.

In step 411, the blank spectrum of step 405 is subtracted from the sample spectrum of step 409 and the resultant spectrum is analyzed to determine the monochloramine concentration change. This monochloramine concentration corresponds to the ammonia (A) in the original sample. Details of the monochloramine spectroscopic analysis are provided in the disclosure with reference to FIG. 6.

In step 413, sulfuric acid from pump 220 is added to achieve a pH of 3 or below, and additional hypochlorite is added from pump 218 if needed to maintain an excess of chlorine. At this pH, ammonia, monochloramine, and dichloramine are all are converted to trichloramine through the reactions of Eq. 2 through Eq. 5.

In step 415, a trichloramine sample spectrum is collected.

In step 417, the blank spectrum of step 405 is subtracted from the sample spectrum of step 415 and the resultant spectrum is analyzed to determine the trichloramine concentration. This trichloramine concentration corresponds to the ammonia plus monochloramine plus dichloramine plus trichloramine (A+M+D+T) in the original sample; ie. $NX_3$ (measured as molar nitrogen) or nitrogen reacted with any combination of hydrogen and chlorine. This method is relatively insensitive to other nitrogen present, such as in the form of nitrates, proteins or amino acids, since these nitrogen sources decompose too slowly to be relevant in the sample period involved of less than 30 seconds. The $NX_3$ concentration is useful, for instance, to plant operators as a diagnostic indicator of ammonia fed through ammonia feed system 111, plus natural aqueous ammonia concentration; i.e. all incoming ammonia available for chlorination, despite variations in dosage pump action, incoming aqueous ammonia already present in the water 101, flowmeter inaccuracies, sodium hypochlorite purity, or liquid ammonia concentration. A precipitous drop in the $NX_3$ concentration would suggest an ammonia feed system failure and may be used to trigger an alarm. Details of the trichloramine spectroscopic analysis are provided in the disclosure with reference to FIG. 9.

Higher chloramine concentrations may be measured by conventional techniques such as disclosed in "Standard Methods of Water and Wastewater Analysis 20th edition" pages 4-45 to 4-46. The preferred method of higher chloramine concentration determination is disclosed in FIG. 5. Under processor control, Cl which is either free or combined as monochloramine, is reacted to $I^-$ to produce iodine whose concentration is determined. The reactions appear to be:

$$Cl_2 + 2KI \text{ - - -} > I_2 + 2KCl \quad (\text{Eq. 6})$$

$$NH_2Cl + H_2O \text{ - - -} > HOCl + NH_3 \quad (\text{Eq. R2})$$

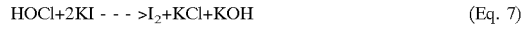

$$HOCl + 2KI \text{ - - -} > I_2 + KCl + KOH \quad (\text{Eq. 7})$$

The pH is then lowered with sulphuric acid which adds H⁺, allowing the Cl in higher chloramines to be reacted, forming more iodine. The reactions appear to be:

$$NCl_3 + H_2O \text{ - - -} > NHCl_2 + HOCl \quad (\text{Eq. R5})$$

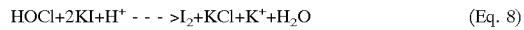

$$HOCl + 2KI + H^+ \text{ - - -} > I_2 + KCl + K^+ + H_2O \quad (\text{Eq. 8})$$

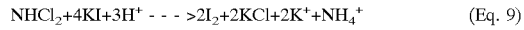

$$NHCl_2 + 4KI + 3H^+ \text{ - - -} > 2I_2 + 2KCl + 2K^+ + NH_4^+ \quad (\text{Eq. 9})$$

Note Eq. R2 is the reverse of Eq. 2, Eq. R5 is the reverse of Eq. 5, and that water acts as a catalyst in the combination of Eq. R5 with Eq. 8. If $I^-$ is in excess, as is preferred, $I_2$ complexes to $I^-$ as the triiodide ion $I_3^-$. The unmodified term "iodine" is used to encompass either $I_2$ or $I_3^-$. (The reactions of Eq. 6, R2, and 7 must occur first; otherwise they will occur at low pH, preventing the differentiation of higher chloramines versus monochloramine or chlorine.) The difference between the high-pH iodine concentration and the low-pH iodine concentration, represents the higher chloramine concentration.

To detail, in steps 501, the analyzer cell 215 is flushed and purged in a similar manner as step 401.

In step 503, a sample is pumped from valve 203 into the analyzer cell 215, and a blank spectrum is collected and stored as a reference.

In step 505, an excess of KI solution is added to the sample with pump 219 and mixed by bubbling. The KI solution may be prepared by mixing 50 grams of KI per liter of deionized water.

In step 507, a delay of about 10 seconds allows reaction of the iodide with chlorine and monochloramine to form iodine, which has a strong UV absorbance. A sample spectrum is taken. Details of the iodine spectroscopic analysis are provided in the disclosure in reference to FIG. 7.

At step 509, the blank spectrum of step 503 is subtracted from the spectrum of step 507, and the result analyzed for iodine, which concentration corresponds to the concentration of chlorine plus monochloramine (C+M).

At step 511, a 10% sulfuric acid in deionized water solution is added from pump 220 to lower the pH to below 4 and mixed by bubbling. More KI may be added with pump 219 if needed to maintain an excess of $I^-$. At this pH, trichloramine quickly backreacts to produce iodine and dichloramine.

At step 513, the sample spectrum is immediately taken, the blank spectrum of step 503 subtracted, and the result again analyzed for iodine, which concentration corresponds to the concentration of chlorine plus monochloramine plus trichloramine (C+M+T). If the chlorination system is known to be under sufficient control that trichloramine will not be produced in significant quantity, this spectrum processing may be skipped, and the trichloramine concentration is assumed to be zero. This step may also be skipped if only the higher chloramine concentration is needed, without differentiating between dichloramine and trichloramine.

At step 515, a two-minute delay is taken. More KI may be added with pump 219 if needed to maintain an excess of $I^-$. Dichloramine, including that from trichloramine decomposition, more slowly decomposes to form chlorine which in turn replaces the $I^-$ to produce iodine. The sample spectrum is taken, the blank spectrum of step 503 subtracted, and the result again analyzed for iodine, which concentration corresponds to the concentration (as molar chlorine) of chlorine plus monochloramine plus trichloramine plus dichloramine (C+M+T+D). If accuracy requires, it is recognized that a slight amount of dichloramine decomposes and is measured in the sampling of step 513. This amount may be extrapolated using the measurement of step 515 and the time between the acid addition and the spectrum sampling of step 513, and corrections made.

At step 517, the various concentrations are computed by the processor 250 (as molar chlorine):

| | |
|---|---|
| dichloramine (D) = | (C + M + T + D from step 515) – (C + M + T from step 513) |
| trichloramine (T) = | (C + M + T + D) – D – (C + M from step 509) |
| higher chloramine = | T + D |
| chlorine (C) = | (C + M + T) – M – T |

Monochloramine (M) concentration is already known, if desired, at step 405, and the ammonia concentration (A) is already known at step 411. As the measurement of step 405 is somewhat noisy, a more accurate monochloramine measurement may be derived by computing:

monochloramine (M) = (A + M + D + T from step 417) – A – D – T

An optimization of the higher chloramine-determining steps may be accomplished by subtracting the sample spectrum of step 507 from the sample spectrum of step 515. The result is analyzed for the change in iodine spectrum, which corresponds to the chlorine released by higher chloramines, and therefore higher chloramine concentration (measured as molar chlorine) of the original sample. With this optimization, the blank spectrum of step 503 is no longer needed if only the concentration of higher chloramines is needed. If the system is known to be in sufficient control that trichloramine is not produced in significant quantity, this concentration of higher chloramines is identical to the dichloramine concentration.

At step 521, the higher chloramine concentration is compared to the ammonia concentration 519 from step 411 to derive an ammonia error signal. Preferably, the comparison is performed by subtracting the ammonia concentration from the higher chloramine concentration; an ammonia error signal greater than zero indicates that more ammonia is needed with respect to chlorine, while an ammonia error signal less than zero indicates that less ammonia is needed with respect to chlorine. A deadband may be employed, so that an ammonia error signal greater than, for example, +0.05 PPM must be measured before the ammonia feed is increased, and an ammonia error signal less than –0.07 PPM must be measured before the ammonia feed signal is decreased. Known downstream sinks of either ammonia or chlorine may alter this comparison, so that the optimal ammonia error signal may be greater or lesser than zero.

Alternatively, the comparison is performed by dividing the higher chloramine concentration by the ammonia concentration to derive an ammonia error signal, with a hypothetical result of unity indicating an optimal feed of ammonia to chlorine. If the measured ammonia concentration is zero, leading to an undefined division by zero, a result of a large number is substituted. An ammonia error signal of greater than unity indicates that more ammonia is needed with respect to chlorine, while an ammonia error signal of less than unity indicates that less ammonia is needed with respect to chlorine. In practice, a deadband may be employed, so that an ammonia error signal greater than, for example, 1.05 must be measured before the ammonia feed is increased, and an ammonia error signal less than, for example, 0.98 must be measured before the ammonia feed signal is decreased. Also, in practice, known downstream sinks of either ammonia or chlorine may alter this ratio, so that the optimal error signal may be greater or lesser than 1.0.

As another alternative, the comparison is performed by dividing the A+M+D+T (or $NX_3$, measured as molar nitrogen) concentration by the chlorine+M+D+T (measured as molar chlorine) concentration to derive an ammonia error signal, with a hypothetical result of unity indicating an optimal feed of ammonia to chlorine. If the measured chlorine+M+D+T concentration is zero, leading to an undefined division by zero, a result of a large number is substituted. An ammonia error signal of greater than unity indicates that more ammonia is needed with respect to chlorine, while an ammonia error signal of less than unity indicates that less ammonia is needed with respect to chlorine. Again in practice, a deadband may be employed, so that an ammonia error signal greater than, for example, 1.05 must be measured before the ammonia feed is increased, and an ammonia error signal less than, for example, 0.98 must be measured before the ammonia feed signal is decreased. Also, in practice, known downstream sinks of either ammonia or chlorine may alter this ratio, so that the optimal error signal may be greater or lesser than 1.0.

Less preferably, the ammonia error signal is derived by including residual chlorine components in the comparison. For instance, the ammonia concentration may be subtracted from, or divided into, (higher chloramines+chlorine, or C+T+D), to derive the ammonia error signal. Also less preferably, the ammonia concentration may be subtracted from, or divided into, (higher chloramines+chlorine+monochloramine, or C+M+T+D; i.e. all chlorination compounds), to derive the ammonia error signal. These signal methods have inferior linearity, but are simpler to derive (steps 507–509 may be skipped) and may provide adequate control. Even less preferably, 'single-ended' signals (not comparing two measured variables, one of which increases while the other decreases) may be used to derive the ammonia error signal while avoiding the limitations of the prior art. For instance, the D, D+T, or D+T+C concentrations may be compared against a numeric constant, such as an operator-entered target value, to determine the ammonia error signal. These signal methods have inferior linearity and range, and are susceptible to drift, but have even simpler derivation and again may provide adequate control.

At step 525, the ammonia error signal is time-conditioned by processor 250 to produce an ammonia feed signal output at step 527. Details of this algorithm are given in the disclosure with respect to FIG. 8. Alternatively, the ammonia error signal is output to an external system for custom control at step 523. Also alternatively, a chlorine error signal is output at step 524, or time-conditioned and output at step 524.

At step 527, the ammonia feed signal is applied over line 150 to an ammonia feed system 111 to raise the concentration of ammonia being mixed with the chlorinated water 101, in response to a signal change indicating a need for a higher ammonia feed with respect to chlorine, at valve 116. Alternatively, a signal may be sent over line 152 to decrease the chlorine feed at valve 115. As the monochloramine concentration is known, an inadequate monochloramine concentration (i.e. underchlorination or more accurately, underchloramination) may be determined by comparing the monochloramine concentration to a numeric constant, such as an operator-entered desired concentration, to derive a monochloramine error signal. If this signal indicates underchloramination, correction is performed by increasing both the ammonia feed signal over line 150, in conjunction with increasing the chlorine feed signal over line 152. If a custom control algorithm is being performed by PLC 158, both the ammonia error signal is output at step 522, and the chlorine error signal is output at step 523, to the PLC 158 for custom control providing optimal monochloramine concentrations, maintaining minimal ammonia or higher chloramine concentrations. Alternatively, the monochloramine error signal may be time-conditioned using the algorithm of FIG. 8, with the result applied to both the ammonia feed signal 150 and the chlorine feed signal 152. In practice, the feed signals may be applied by transmitting over serial line 256 to the programmable-logic controller 158 which ultimately controls the feed valves, by converting to an analog voltage, or a variety of other methods depending on the actual control structure involved.

At step 529, the resultant concentrations of ammonia, ammonia available for chlorination, chlorine, monochloramine, trichloramine, and dichloramine, as well as the ammonia feed signal, may be output on display 252 to the operator, logged, strip-charted, or otherwise archived for quality-control or compliance purposes. Alarms, such as an out-of-range condition or sudden change in any of the various concentrations, may also be triggered at this step, as are well known in the art.

As conditions permit, as at night when water demand is low and fast sampling is not needed, the analyzer 200 may periodically be cleaned by flushing with cleaning solution through valve 209, and recalibrated by repeating steps 401–517 for deionized water injected through valve 211 for calibration of a zero-absorbance spectrum, by injecting a known ammonia solution through valve 207 for calibration of the steps of FIG. 4, and by injecting an incoming water sample through valve 201 for calibration of monochloramine determination of step 405. Calibration of the steps of FIG. 5 may be performed by producing iodine for calibration by injecting excess $H_2SO_4$ from pump 220 and NaOCl from pump 218, and an accurate quantity of KI from pump 219 into the analyzer cell 215 for quantitative production of iodine, and subsequent spectroscopic measurement.

Figure 6:
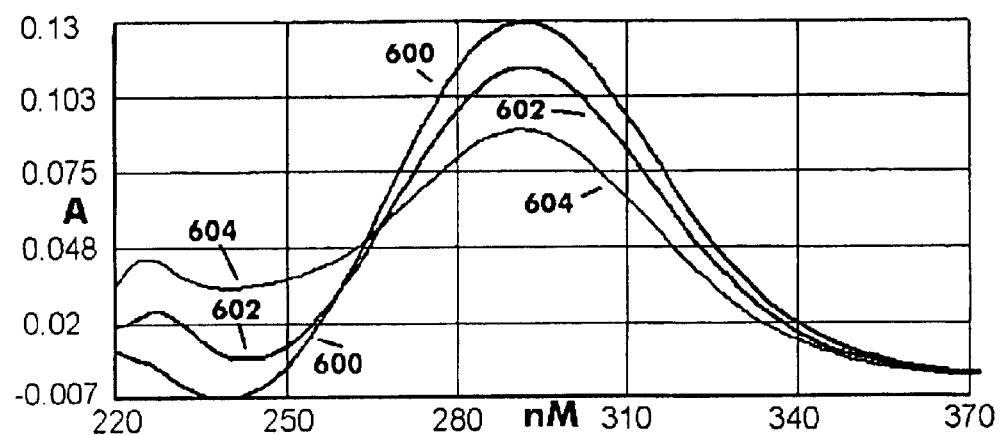
FIG. 6 shows a spectrum of monochloramine over a range of concentrations.

A spectrum of monochloramine at various concentrations in water at pH 9 is shown in FIG. 6. Curves 600, 602, and 604 indicate the absorbance of chlorine at 12 milligrams/liter and monochloramine derived from ammonia concentrations of 0, 0.2, and 0.4 ppm. In realistic operation, the curve will be corrupted somewhat by impurities. Determination of ammonia concentration is accomplished by adding NaOCl to convert the ammonia to monochloramine at step 407, taking a monochloramine spectrum at step 409, and subtracting the blank spectrum from the monochloramine spectrum step 411. The difference in spectra will be due to the creation of monochloramine, apparent by the increase in absorbance at 230 nm, while the spectra of impurities will cancel out. The absorbance at 295 nm is due to the $OCl^-$ ion; the absorbance decreases since the $OCl^-$ ion is consumed producing monochloramine. The pattern recognition technique known as Principle Component Analysis (PCA) is used by the processor 250 to separate the monochloramine spectrum from the excess $OCl^-$ spectrum and determine the monochloramine concentration. PCA is described in detail in "Principal Component Analysis" by I. Jolliffe, Springer-Verlag, N.Y., 1986.

Figure 7:
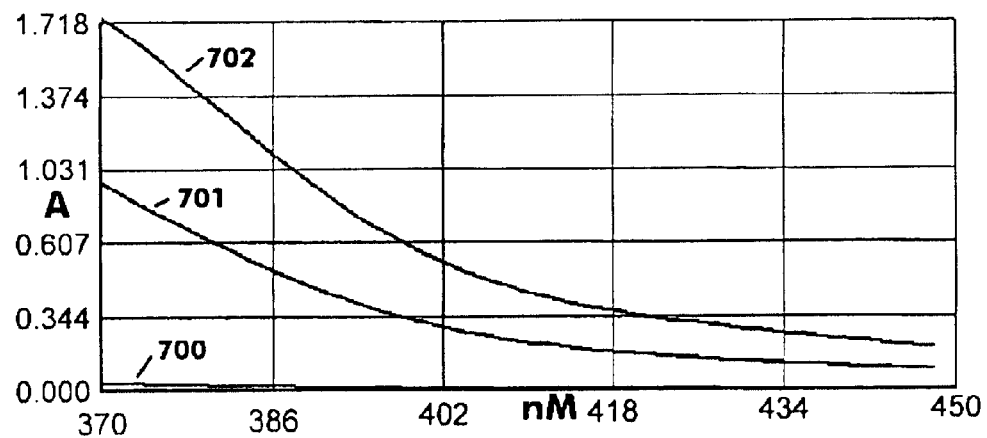
FIG. 7 shows a spectrum of iodine over a range of concentrations.

A spectrum of iodine absorbance at various concentrations in water is shown in FIG. 7. Curves 700, 701, and 702 indicate the absorbance of iodine corresponding to concentrations of 0, 1, and 2 milligrams of chlorine per liter. Note that at 370 nM and 2 milligrams/liter, the absorbance of about 1.7 corresponds to 98% of light absorbed, a very strong signal. PCA is again performed by the processor 250 on the spectra to determine the iodine concentration.

A spectrum of trichloramine absorbance at various concentrations in water is shown in FIG. 9. Curves 900, 902, 904, and 906 indicate the absorbance of trichloramine corresponding to concentrations of 0, 0.2, 0.4 and 0.6 milligrams of ammonia per liter. The trichloramine spectrum is characterized by a strong absorbance around 230 nM. PCA is again performed by the processor 250 on the spectra to determine the trichloramine concentration.

The utility of the ammonia feed signal is disclosed by referring back to FIG. 1. Water 101 enters the plant 100, receives feeds of chlorine 102 and ammonia 113, and may be mixed and aerated 104, filtered 106, fluoridated 108, or receive various other treatments. During these treatment steps, some chlorine is consumed by, for instance, killing microbes or reacting to protein or iron, and the ammonia and remaining chlorine react to form chloramines. Since these reactions take time, samples are taken downstream at a sample point 109 where the reactions are known to be substantially complete. The actual location of this point will vary depending on the installation; if too far downstream, control speed suffers; if too far upstream, reactions are not yet complete. The sample water is piped to the analysis system 200 and analyzed. Control changes based on this analysis are transmitted to ammonia feed valve 116 and/or chlorine valve 115. A feed change at valves 115 or 116 will not be evident at sample point 109 until the resultant water has flowed the intervening distance.

To prevent multiple adjustments from occurring before the result of the first adjustment has reached the sample point 109, the ammonia error signal must be time-conditioned to produce the ammonia feed signal. This timing could be computed by the PLC 158 sending the water flow to the analyzer 200 over serial line 256, in conjunction with the known distance from the chemical feed points to the sample point 109. A simple time-conditioning algorithm to prevent overreaction would be to delay sampling (i.e. a timeout) until the result of the previous adjustment was known to have reached the sample point 109. The timeout could be fixed, such as to the longest contemplated transit time of the water, but preferably would vary depending on, for instance, the installation, and the water flow, which in turn depends on water demand at that time. In situations where the incoming water 101 changes composition slowly, as if originating from an underground aquifer, the ammonia error signal may be output unchanged as the ammonia feed signal, a timeout taken, and the analysis repeated. Alternatively, the ammonia error signal could be transmitted over line 256 to the PLC 158 operating the plant 100, which performs a custom control algorithm optimized for that facility. In situations where the incoming water 101 changes composition quickly, as if originating from a river, more adaptable control is preferred.

Figure 8:
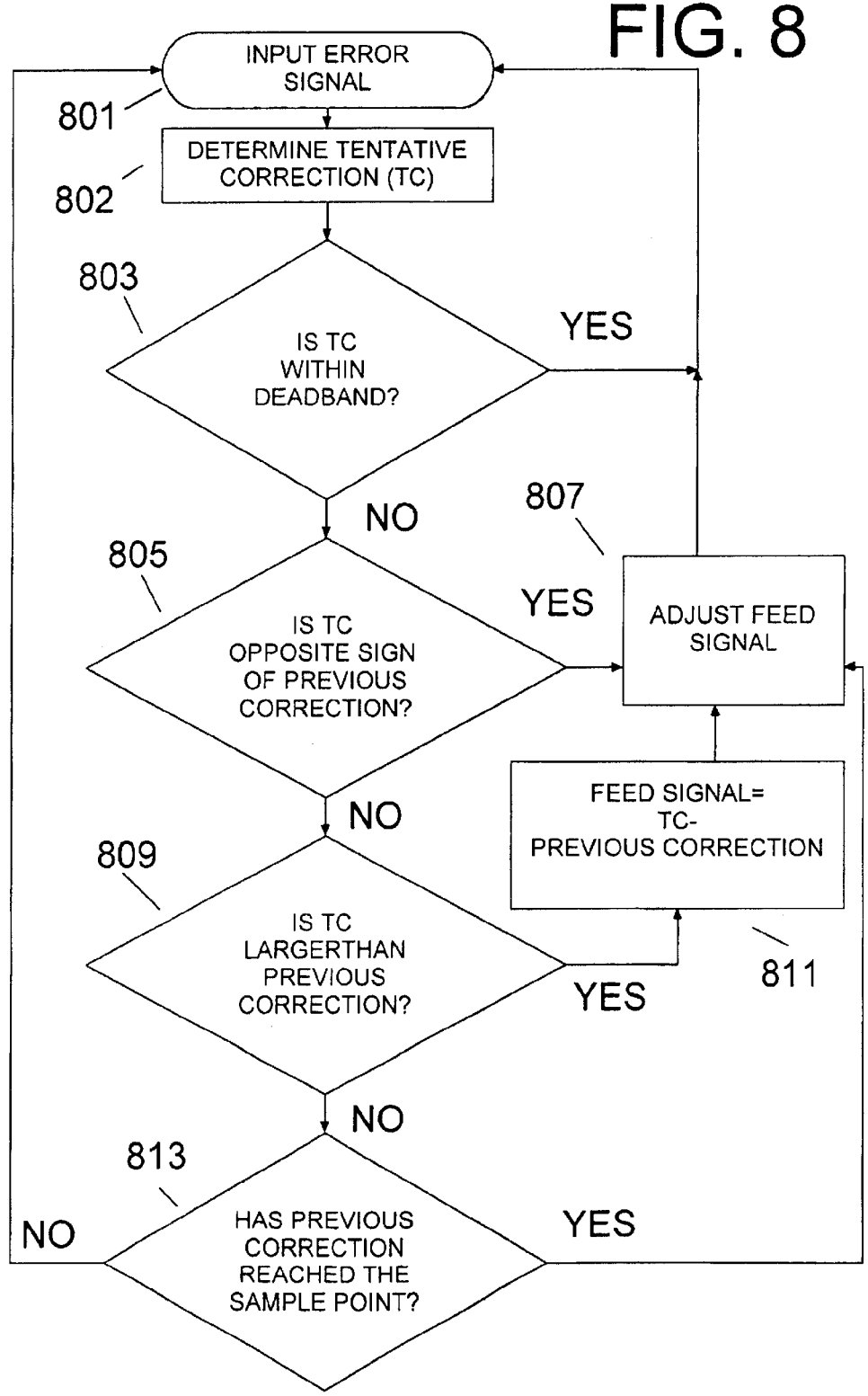
FIG. 8 shows a flowchart of the process of determination of an ammonia feed signal.

A preferred control method is disclosed in FIG. 8. A preferred control system provides faster response to varying inputs, while maintaining stability. Some change at the input may be transient (a 'spike' such as increased mud resulting from a ship dropping anchor near a water inlet), returning quickly to a baseline. A simple timeout may correct for an input change, while the input spontaneously returns to baseline. The result is a double-correction (the spontaneous return plus the programmed correction) and operation outside the desired control range. Since the control system is performing a timeout and ignoring the input, this out-of-control operation is not corrected. Or some change may be gradual and large in magnitude, such as increased leaf-protein after an autumn rainstorm. A simple timeout may react to the beginning of a change, and ignore continued change during the timeout. The preferred control method gives superior response to transients by monitoring for overshoots and continued change during the timeout.

Figure 5:
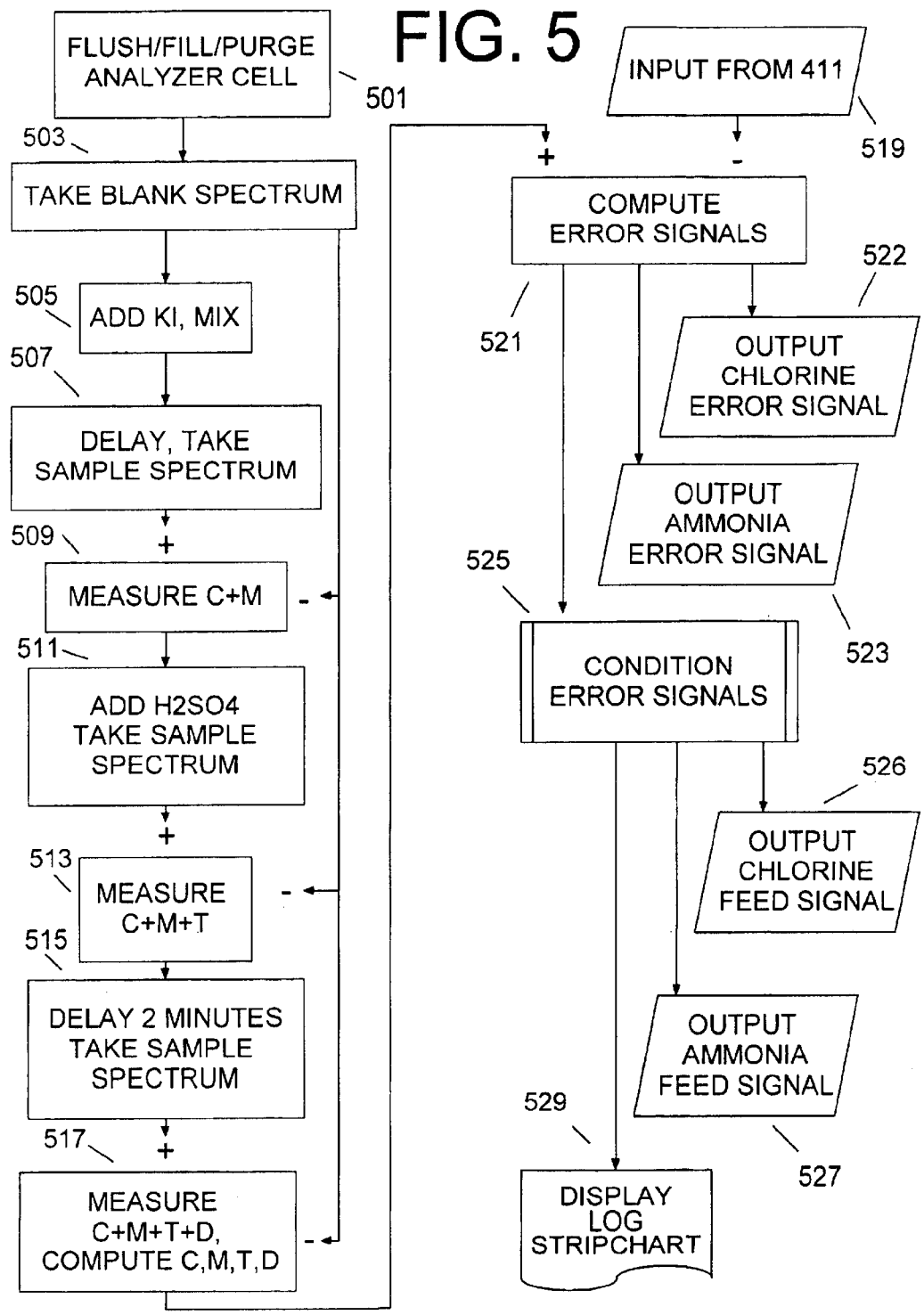
FIG. 5 shows a flowchart of the process for determining higher chloramine concentration.

At step 801, the ammonia error signal is input from step 523 of FIG. 5, and converted to a tentative correction at step 802, where the tentative correction represents the difference between the current ammonia error signal and the previous ammonia error signal. At step 803, control returns to step 801 unless the tentative correction is outside a deadband; i.e. the tentative correction is above noise level. At step 805, the tentative correction is compared to the previous correction. If the previous and tentative corrections are opposite in sign, the previous correction is already known to be excessive (i.e. the input is spontaneously returning to baseline), whether the timeout has expired or not. The tentative correction is therefore executed at step 807. Otherwise, the tentative correction is compared to the previous correction at step 809. If the previous correction is smaller, it is known to be inadequate; i.e. the input is continuing to change. The additional correction is computed by subtracting the previous correction, which has not yet flowed to the analyzer, from the tentative correction and applying the additional correction at step 811. Otherwise, a check is made at step 813 as to whether the result of the previous change has reached the sample point; i.e. the timeout has expired. If the timeout has expired, the tentative correction is made at step 807. Otherwise, control is returned to step 801 to continue monitoring.

The invention is not limited to the specified methods of determining the ammonia or higher chloramine concentrations, or the specified order of steps in the methods. In particular, the ammonia concentration is disclosed as being determined before the higher chloramine concentration determination, although the order of determination is arbitrary and could be reversed. Nor must the ammonia-determining and chloramine-determining steps be alternated; if, for example, ammonia concentrations are found to be varying quickly, the steps of FIG. 4 could be executed multiple time for each execution of the steps of FIG. 5. Also, NaOH and EDTA are added, and a blank spectrum taken, during the ammonia-determining step. As NaOH and EDTA do not interact and do not affect the blank spectrum, these steps could be performed in any order. Other alkalis besides NaOH could be used, for instance NaOCl which would then double as an alkali and a hypochlorite donor. KI is illustrated as an $I^-$ donor, although other reagents such as NaI would perform the needed function. Although an array sensor with, for example, 256 points, is preferred for spectroscopic analysis, the array sensor could be replaced by a point sensor movable with respect to the monochromator, to sequentially sample various points in the spectrum. In this or other situations, the strobe could be replaced by some other light source such as a mercury lamp. The array sensor could also be replaced by a multitude of fixed point sensors sampling predetermined wavelengths, typically resulting in a spectrum with a far lesser, but still useful, number of points. In this case of a multitude of fixed point sensors, the monochromator could be replaced by optical filters passing light to each of the fixed point sensors, such that each fixed point sensor measures a different portion of the spectrum without the need for a separate monochromator. Although the control algorithm of FIG. 8 is disclosed with respect to ammonia, the algorithm is applicable to monochloramine or chlorine control. More generally, chlorine concentration is preferably determined by conversion to trichloramine or iodine with UV spectroscopic measurement; however chlorine concentration could be determined, for instance, by the well-known DPD reaction, as described in U.S. Pat. No. 6,180,412, issued Jan. 30, 2001 to Kroll, which uses visible rather than UV spectroscopy. Ammonia concentration could be determined by using an ammonia-sensitive electrode as described in "Standard Methods of Water and Wastewater Analysis 20th edition" pages 4-78 through 4-79, or by the well-known modified phenate method or salicylate method, or other methods. Similarly, higher chloramine concentration is preferably determined by a replacement reaction producing iodine with subsequent UV spectroscopy; however, other higher chloramine-determining methods could be used, or iodine concentration could be measured by other methods such as the well-known starch-iodine reaction. Concentrations and equations are generally shown in the disclosure as molar quantities for simplicity, although it is to be understood that measurement by weight, or by originating chemical (i.e. Cl measured as weight of NaOCl) is equivalent. The various control signals, for instance the ammonia error signal, are described as increasing in value to indicate a need to increase a flow; however equivalent operation would result if the signal decreased in value to indicate a need to increase a flow. The ammonia feed signal preferably controls an ammonia feed system, raising ammonia concentrations when the ratio of ammonia to higher chloramines is inadequate; however balance may also be achieved in this situation by the ammonia feed signal causing a decrease in the chlorine feed. The invention is preferably practiced using a single analyzer cell; however multiple analyzer cells could be utilized to measure ammonia and higher chloramines in parallel, if higher analysis speed is essential. These are other variants are within the spirit and scope of the claims below.

What is claimed is:

1. A method of determining the optimal chlorination of a supply of water containing ammonia and chlorination compounds, comprising the steps of:
   a. raising the pH of a first sample of the water to at least 8 and determining the molar ammonia concentration in the supply of water;
   b. Determining and summing the molar concentrations of $Cl_2$, plus hypochlorite, plus hypochlorous acid, plus monochloramine in a second sample of the water, to yield a first concentration;
   c. lowering the pH of the second sample of the water to less than 3 and determining and summing the molar concentrations of $Cl_2$, plus hypochlorite, plus hypochlorous acid, plus monochloramine, plus dichloramine multiplied by two, plus trichloramine multiplied by three, in the supply of water, to yield a second concentration;
   d. subtracting the first concentration from the second concentration to derive a higher-chloramine chlorine concentration;
   e. and performing a comparison of the higher-chloramine chlorine concentration to the ammonia concentration to derive an ammonia error signal.

2. The method of claim 1, where the higher-chloramine chloride concentration is derived by:
   a. measuring the absorbance of iodine produced by the reaction of iodide with chlorine and monochloramine to yield a first spectrum;
   b. measuring the absorbance of iodine produced by the reaction of iodide with chlorine and monochloramine and higher chloramine to yield a second spectrum;
   c. and subtracting the first spectrum from the second spectrum to produce a third spectrum, and analyzing the third spectrum to derive the higher-chloramine chlorine concentration.

3. The method of claim 1, where the comparison of the higher-chloramine chlorine concentration to the ammonia concentration is performed by dividing the molar higher-chloramine chlorine concentration, by the molar ammonia concentration.

4. The method of claim 1, where the comparison of the higher-chloramine chlorine concentration to the ammonia concentration is performed by subtracting the molar ammonia concentration from the molar higher-chloramine chlorine concentration.

5. The method of claim 1, where a single analyzer cell is used for determining the ammonia concentration and the higher-chloramine chlorine concentration in the water.

6. The method of claim 1, additionally comprising the steps of:
   f. determining the monochloramine concentration in the water;
   g. performing a comparison of the monochloramine concentration to a deadband to derive a monochloramine error signal;
   h. in response to a monochloramine error signal indicating underchloramination, increasing the value of the ammonia error signal and increasing the value of a previously-set chlorine feed signal.

7. The method of claim 6, where the monochloramine concentration is determined by converting the monochloramine to trichloramine.

8. The method of claim 1, additionally comprising the step of:
   f. applying the ammonia error signal to an ammonia feed system which feeds a higher ratio of ammonia with respect to chlorine to the water in response to a value of ammonia feed signal indicating a need for a higher ratio of ammonia with respect to chlorine.

9. The method of claim 1, additionally comprising the steps of:
   f. time-conditioning the ammonia error signal to derive an ammonia feed signal;
   g. applying the ammonia feed signal to an ammonia feed system which feeds a higher ratio of ammonia with respect to chlorine to the water in response to a value of ammonia feed signal indicating a need for a higher ratio of ammonia with respect to chlorine.

10. A method of controlling the chlorination of a supply of water containing ammonia and chlorination compounds, comprising the steps of:
    a. transporting (103) a first sample of the water (101) from a sample point to an analyzer cell (213);
    b. adding a sufficient amount of alkali to the first sample to raise the pH to at least 8, adding a sufficient amount of EDTA to the first sample to prevent precipitation of hard-water components (403), and measuring and storing a first blank spectrum of the first sample (405);
    d. adding an excess of hypochlorite to the first sample (407);
    e. waiting for the hypochlorite to react to ammonia in the first sample to form monochloramine;
    f. measuring and storing a monochloramine spectrum of the monochloramine (409);
    g. subtracting the first blank spectrum from the monochloramine spectrum to derive an ammonia spectrum (411);
    h. analyzing the ammonia spectrum to determine the molar ammonia concentration in the first sample (413);
    i. transporting a second sample of water to the analyzer cell (501);
    j. adding an excess of $I^-$ to the second sample (507), and measuring and storing a second blank spectrum of the second sample (509);
    k. adding a sufficient amount of acid to the second sample to drop the pH of the second sample to less than 4 (511);
    l. waiting for the $I^-$ to react to chlorination compounds producing iodine;
    m. measuring an iodine spectrum of the iodine (513);
    n. subtracting the second blank spectrum from the iodine spectrum to obtain a chlorination compound spectrum (517);
    o. analyzing the chlorination compound spectrum to determine the molar higher-chloramine chlorine concentration (517) in the second sample;
    p. comparing the molar higher-chloramine chlorine concentration to the molar ammonia concentration to derive a comparison, and deadbanding said comparison to derive an ammonia error signal (521);
    q. time-conditioning (525) the ammonia error signal to derive an ammonia feed signal (527), said time-conditioning comprising;
    r. comparing the ammonia feed signal to a previous ammonia feed signal to derive a tentative correction (802);
    s. if the tentative correction is the opposite sign of a previous correction (805), applying the tentative correction (807) to an ammonia feed system (111), recording the tentative correction as the previous correction, and returning to step a;
    t. if the tentative correction is of larger magnitude than the previous correction (809), applying the tentative correction minus the previous correction (811) to the ammonia feed system, recording the tentative correction as the previous correction, and returning to step a;
    u. if a timeout (813) has occurred since the last correction, applying the tentative correction to the ammonia feed system and recording the tentative correction as the previous correction;
    v. and returning to step a.

11. A method of determining the optimal chloramination of a supply of water containing ammonia and chlorination compounds, comprising the steps of:
    a. Determining and summing the molar concentrations of $Cl_2$, plus hypochlorite, plus hypochlorous acid, plus monochloramine in a sample of the water, to yield a first concentration;
    b. lowering the pH of the sample of the water to less than 3 and determining and summing the molar concentrations of $Cl_2$, plus hypochlorite, plus hypochlorous acid, plus monochloramine, plus dichloramine multiplied by two, plus trichloramine multiplied by three, in the supply of water, to yield a second concentration;
    c. subtracting the first concentration from the second concentration to derive a third concentration;
    d. and performing a comparison of the third concentration to an operator-entered target value to derive an ammonia error signal.

12. The method of claim 11, where a single analyzer cell is used for determining the first concentration and the second concentration.

13. A method of determining the optimal chlorination of a supply of water containing ammonia and chlorination compounds, comprising the steps of:

a. raising the pH of a sample of the water to at least 8 and measuring the molar monochloramine concentration in the supply of water;
b. adding iodide to a second sample of the water, and measuring the iodine spectrum to yield a first molar iodine concentration;
c. lowering the pH of the second sample of the water to less than 3 and measuring the iodine spectrum to yield a second molar iodine concentration;
d. subtracting the first concentration from the second concentration to derive a higher-chloramine-derived molar iodine concentration;
e. and performing a comparison of the higher-chloramine-derived molar iodine concentration to the molar monochloramine concentration to derive an ammonia error signal.

14. The method of claim 13, where a single analyzer cell is used for determining the ammonia concentration and the higher chloramine concentration in the water.

15. The method of claim 13, additionally comprising the steps of:
f. performing a comparison of the molar monochloramine concentration to a deadband to derive a monochloramine error signal;
g. in response to a monochloramine error signal indicating underchloramination, increasing the value of the ammonia error signal and increasing the value of a previously-set chlorine feed signal.

16. The method of claim 13, additionally comprising the steps of:
f. time-conditioning the ammonia error signal to derive an ammonia feed signal;
g. applying the ammonia feed signal to an ammonia feed system which feeds a higher ratio of ammonia with respect to chlorine to the water in response to a value of anunonia feed signal indicating a need for a higher ratio of ammonia with respect to chlorine.

* * * * *